US006179793B1

(12) United States Patent
Rothman et al.

(10) Patent No.: US 6,179,793 B1
(45) Date of Patent: *Jan. 30, 2001

(54) CARDIAC ASSIST METHOD USING AN INFLATABLE VEST

(75) Inventors: Neil S. Rothman; Mark Gelfand, both of Baltimore, MD (US); Daniel Burkhoff, Tenafly, NJ (US); Myron L. Weisfeldt, Irvington, NY (US)

(73) Assignee: Revivant Corporation, Sunnyvale, CA (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/006,823

(22) Filed: Jan. 14, 1998

(51) Int. Cl.[7] ........................ A61H 31/00; A61B 5/0245

(52) U.S. Cl. ............................ 601/44; 600/17; 600/510; 600/521

(58) Field of Search .................................. 601/1, 41, 43, 601/44, 105, 106, 148–152; 600/509, 510, 520, 521, 17, 16, 484

(56) References Cited

U.S. PATENT DOCUMENTS

| | | | |
|---|---|---|---|
| 3,835,845 | 9/1974 | Maher . | |
| 4,077,402 | 3/1978 | Benjamin, Jr. et al. . | |
| 4,397,306 | 8/1983 | Weisfeldt et al. . | |
| 4,424,806 * | 1/1984 | Newman et al. | 601/41 |
| 4,676,232 * | 6/1987 | Olsson et al. | 601/41 |
| 4,928,678 | 5/1990 | Halperin et al. . | |
| 4,971,042 | 11/1990 | Lerman . | |
| 5,020,516 | 6/1991 | Biondi et al. . | |
| 5,218,954 | 6/1993 | van Bemmelen . | |
| 5,490,820 | 2/1996 | Schock et al. . | |
| 5,514,079 | 5/1996 | Dillon . | |

FOREIGN PATENT DOCUMENTS

96/28128 * 9/1996 (WO) .

OTHER PUBLICATIONS

Chandra et al., "Vital Organ Perfusion During Assisted Circulation by Manipulation of Intrathoracic Pressure", Circulation, pp. 279–286, Jul. 1991.*

* cited by examiner

*Primary Examiner*—Danton D. DeMille
(74) *Attorney, Agent, or Firm*—K. David Crockett, Esq.; Crockett & Crockett

(57) ABSTRACT

A method is disclosed for inflating an inflatable vest to assist the heart in patients suffering from heart failure. The inflation of the vest is synchronized with on-set of the systole phase of the heart, when the left ventricular compresses to force blood out of the heart and through the aorta. The inflated vest compresses the patient's chest and increases the intrathoracic pressure. This increase in pressure assists the heart in moving blood out of the heart and through the aorta. In addition, the vest is arranged to leave the patient's abdomen free of restraint so that the increase in intrathoracic pressure due to the vest moves blood into the abdomen, and to allow the abdomen to dynamically recoil in response to the vest inflation. In addition, ECG signals from electrodes applied to the patient are processed to trigger the vest inflation in real time with the current heartbeat cycle, such that the vest inflation is triggered when the heart begins to contract. A controller provides an adjustable signal blanking period to avoid noise components following the QRS complex.

3 Claims, 6 Drawing Sheets

CARDIAC ASSIST METHOD USING AN INFLATABLE VEST

TECHNICAL FIELD

The present invention relates to the medical field of cardiopulmonary assist treatment, and especially to cardiac assist methods using external body compression to improve the vascular blood flow and pressure in patients with weak or deteriorating hearts.

BACKGROUND

I. Heart Failure—Need for Circulatory Assist

There is a need for medical equipment and methods for treatments that assist a beating heart of a patient suffering from heart disease or other weakened heart condition. When a heart becomes diseased or weak, the heart muscle deteriorates. The weakened heart muscle strains to pump sufficient amounts of blood through the patient's vascular system. The strain placed on the already-weak heart can lead to further deterioration and weakening of the heart. Treatments that assist a weakened heart to pump blood can be therapeutic by relieving some of the strain on a laboring, weakened heart.

The heart functions as two pumps in series. The right ventricle forces blood through the lungs into the left ventricle, and the left ventricle forces blood through the systemic circulation into the right ventricle. Small, but significant contributions to blood flow are also made by the skeletal muscle pump and the respiratory pump. In addition, the major periods of the cardiac cycle are diastole, during which the ventricles fill, and systole during which the ventricles eject blood.

To meet the demand for blood in a patient's vascular system, a weak heart increases its beat rate and devotes an increasing portion of its time and energy to pumping blood. The weak heart attempts to compensate for its weakness by working harder to pump blood through the vascular system. The straining heart diverts its time and energy away from sustaining itself with blood. In particular, the heart cuts short its rest stages during which blood normally flows into the heart muscle through the coronary arteries. When the rest stages become too short, the heart does not receive enough blood to sustain its already-weakened condition. By depriving itself of adequate amounts of blood, the heart contributes to its own deterioration. Accordingly, a weakened heart may deteriorate in a perilous cycle that increasingly strains the heart to pump blood and further reduces the blood supplied to the heart itself. This cycle can result in rapid heart deterioration (within a few hours or days) that leads to the irreversible failure of vital organs including the heart itself and possibly death.

A method to treat heart disease and other conditions in which a beating heart is weakened or over-strained is to assist the heart in pumping blood to the vascular system of the patient. By assisting the flow of blood, the strain (also referred to as load) on the heart can be artificially reduced.

The heart ejects blood from its left ventricular LV chamber into the aorta which leads to the vascular system. The "load" on the heart is the power required by the heart to eject blood from the LV chamber and aorta. Cardiac assist treatments reduce the load on the heart. When a weakened heart ejects blood against a reduced load, the heart can successfully evacuate more blood from the LV chamber and heart than would be evacuated without an assist volume. During each heart 'stroke' the heart ejects more blood which leads to the increase of total blood flow, i.e., cardiac output, from the heart and through the vascular system.

In addition, by reducing some of the pumping load, the heart can devote more of its resources and time to providing blood to its own coronary arteries. Coronary arteries stem from the segment of the aorta that is closest to the heart and provide blood to the heart muscle. When the coronary arteries and muscle have sufficient blood flow, the heart has the ability to heal itself.

The heart often is prevented from healing itself when caught in the dangerous cycle of ever deteriorating and increasing strain. A cardiac assist treatment breaks this cycle by relieving the heart of some of its strain and reducing the load on the heart. Cardiac assist can treat a heart condition by relieving the load on the heart and allowing the heart to heal itself. Even if the heart is unable to heal itself, cardiac assist is beneficial because it prevents further deterioration and total heart failure, e.g., heart stoppage, until some other treatment, such as heart surgery, can be applied.

II. Existing Methods For Cardiac Assist

Ventricular Assistance has been attempted and, in some cases, accomplished by the following methods set forth in TABLE A:

TABLE A

| |
|---|
| Intra-aortic balloon Pump (IABP) |
| Heart bypass (Left Ventricular Assist Devices - LVAD and Right Ventricular Assist Devices RVAD) |
| External upper body compression. |
| Cardiopulmonary bypass also known as heart-lung machine |
| Veno-arterial and Veno-venous bypass. |
| External Leg Counterpulsation. |
| Direct Mechanical Pressure on Heart. |

Of all the methods listed in Table A, IABP is the method most commonly used as a clinical treatment. IABP counterpulsation is a method of providing temporary circulatory assistance to a failing and/or ischemic heart by providing reduced afterload and increased coronary perfusion pressure. In IABP, a balloon catheter is routed through the femoral artery, and positioned in the descending thoracic aorta with the tip of the catheter below the branches of the arteries that feed the heart (coronary) and brain (carotid).

The IABP device is synchronized with an ECG or arterial pulse tracing so that the balloon is rapidly inflated with an inert gas (helium) during the diastole phase of the heart cycle, and is rapidly deflated just before the onset of systole phase. The inflation of the balloon during diastole elevates the blood pressure in the aorta and drives blood into the heart muscle via the coronary arteries. As the balloon is rapidly deflated during systole, a low pressure zone is generated in the aorta. The aorta is, in effect, a large elastic vessel that stores a relatively-large volume of oxygenated arterial blood between heartbeats. The elastic aorta expands, during each heart cycle, to accommodate the added volume of blood called 'stroke volume' ejected from the left ventricle and stored between heartbeats. The elasticity of the aorta resists expansion and, thus, the increased volume of blood pumped from the left ventricle. The resistance from the aorta is in proportion to the initial volume of the aorta, to which the 'stroke volume' is added. The power applied by the left ventricle as it ejects blood is, in part, used to overcome the elastic resistance of the aorta and to push out the stroke volume of blood left in the aorta from the prior heartbeat cycle.

The balloon catheter used with IABP assists the heart by relieving the heart of some of the work of moving the stroke volume of blood out of the aorta to receive a new stroke volume. IABP displaces some of the volume of blood in the aorta by inflating the balloon with compressed gas to displace the stroke volume blood. By collapsing the balloon just before the left ventricle starts to eject blood, IABP creates a 'void' in the aorta, which void is, at least partially, retained as a new stroke volume of blood is ejected from the left ventricle into the void left in the aorta. The void formed in the aorta by IABP reduces the tension of aortic walls and assists the left ventricle in its effort to eject blood by reducing the elastic resistance from the aorta to the stroke volume.

IABP has difficulty keeping up with the rapid heart rates associated with heart failure. When the cardiac cycle is shortened, the duration of diastole is reduced dramatically. The best modern IABP are believed to inflate the balloon in 120 ms minimum and deflate it in another 120 ms. These inflation and deflation rates are too slow to provide effective cardiac assist during each heartbeat cycle at high heart rates. IABP techniques may skip the inflation of the balloons during some heartbeats to facilitate synchronization with the heart cycle.

Other disadvantages of IABP balloon catheters are that they are invasive, require a surgical procedure for use and can be placed only by a specially trained interventional cardiologist, and can result in significant complications, such as amputation of the leg because the catheter prevents blood flow in the femoral artery.

A non-invasive cardiac assist alternative to IABP used in clinical practice is external leg counterpulsation. Examples of external leg counterpulsation are shown in U.S. Pat. Nos. 5,514,079, 5,218,954, 4,077,402 and 3,835,845; and EPO patent application No. 0 203 310 A2. Modern enhanced external counterpulsation involves the use of a device to inflate and deflate a series of compressive cuffs wrapped around a patient's calves, lower thighs, and upper thighs. Inflation and deflation of the cuffs are modulated by the cardiac cycle as monitored by computer-interpreted ECG signals.

During the diastole phase of the heart cycle, the cuffs inflate sequentially from the calves proximally, resulting in augmented diastolic central aortic pressure and increased coronary perfusion pressure. Rapid and simultaneous decompression of the cuffs at the onset of systole permits systolic unloading and decreased cardiac workload. The compression of the legs during heart diastole increases the coronary perfusion pressure gradient and coronary flow. The rapid decompression of the legs during systole reduces systolic arterial pressure which reduces the load on the heart.

The use of external leg counterpulsation is likely to encounter difficulties when used in acute heart patients or patients with severe heart failure. In response to the cardiogenic shock state that occurs during severe heart failure, the body initiates a number of compensatory mechanisms which seek to restore circulatory homeostasis. Skin, skeletal muscle, and kidney vascular beds undergo vasoconstriction to maintain mean arterial pressure and to preserve coronary and cerebral perfusion. Vasoconstriction reduces the blood flow through the legs and, thus, reduces the potential benefit achieved by the cuffs applied to the legs and other extremities in external counterpulsation treatments.

Moreover, an increase in sympathetic tone increases the heart rate and myocardial contractility, thereby maximizing cardiac output. It is highly unlikely that an external counterpulsation system can sequentially inflate and deflate a series of leg cuffs in the short cycle time of a rapid heartbeat. In addition, at high heart rates diastolic perfusion plays a lesser role and systolic perfusion (normally insignificant) starts to play a greater role in total coronary flow. Counterpulsation (by external leg compression or by intra-aortic balloon) can only increase coronary diastolic flow. Accordingly, counterpulsation does not assist with systolic perfusion.

In addition, current leg counterpulsation devices from CardioMedics and Vasomedical weigh approximately 250 lbs. and require 20 Amps AC current to operate. Placement of cuffs on the patient requires substantial time and equipment that may not be available during a heart failure emergency.

Another treatment for assisting a beating but weak heart is to externally compress a portion of the chest, thorax and/or abdomen of a patient's body. Examples of these external compression techniques are disclosed in U.S. Pat. Nos. 4,928,674, 4,971,042, 4,397,306, 5,020,516 and 5,490,820. The compression is applied to force blood out of the compressed region of the body and into other regions of the patient's vascular system. The external compression must be synchronized with the patient's beating heart, which is itself pumping blood, albeit at a reduced capacity and pressure. External compression treatment assists the heart by reducing the pumping load on the heart. When partially relieved of its load, the heart is able to increase the amount of blood ejected with each stroke and to allow blood to better circulate through its own muscle tissue between strokes.

There are some apparent advantages to cardiac assist by external compression relative to balloon catheters. For example, external compression does not require surgery and sterile conditions, as does IABP. External compression generally is not associated with risks of injury, and can be applied in emergency conditions, which often occur outside of a surgical room or intensive care units in the hospital. Despite these apparent advantages of external compression and the long-felt need for better cardiac assist treatments, there have been no successful cardiac assist treatments to humans using external compression.

Use of external chest compression during systole to unload the heart is counterintuitive. It is intuitive to apply counterpulsation to a patient's extremities to force blood towards a weakened heart without applying external compressive forces to the heart. In contrast to counterpulsation techniques, external chest compression applies pressure directly to the heart. One would expect that compression of the chest directly during systole would build up pressure inside the thorax (Intrathoracic Pressure—ITP) at the same time as the failing heart is struggling to eject blood into aorta. This rise of ITP would appear to be translated to the heart and aorta, and result in an increase in the systolic pressure that is commonly perceived as a measure of 'afterload' that determines the work that the left ventricle has to perform to move blood. Accordingly, it would appear that external chest compression would increase the workload placed on a heart and would not provide any cardiac assist. However, this analysis does not take into account several factors including:

(a) The ITP does not primarily determine the workload on the heart. Rather, the wall tension of the heart muscle and the elastic resistance of the great thoracic vessels determines the workload of the heart. The internal resistance to coronary blood flow into the heart muscle is influenced by the volume of the distended heart and the blood pressure gradient across the heart wall (transmural pressure).

(b) When the thorax is compressed through external compression, the transmural pressure (Ptm) across the heart wall is the difference between intraventricular pressure (Plv) in the heart and the intrathoracic pressure (Ptm=Plv−ITP). The transmural pressure is indicative of the tension in the heart wall and, thus, indicates the workload on the heart. The transmural pressure is not determined by the difference between intraventricular pressure and atmospheric pressure.

(c) The heart is completely contained within the thoracic cavity and is approximately uniformly affected by the rise of ITP. Accordingly, increasing ITP does not produce blood pressure gradients within the heart. The aorta extends from the thorax and transverses the diaphragm. The aorta is only partially affected by the ITP change. Accordingly, blood in the aorta will be pushed across the diaphragm and into the abdomen when ITP increases.

(d) ITP is not uniformly distributed as a function of time and position inside the thorax, during the periods of chest compressions.

Under conditions of rapid chest compression and decompression at rates of 60 to 160 beats per minute (such as would occur in cardiac assist treatments), ITP 'fluid pressure waves' are generated inside the chest cavity. These fluid pressure waves cause the distribution of intrathoracic pressure to vary across the inside of the chest cavity at any given time during the chest compression cycle. Animal research has indicated that during rapid chest compressions, the inertia of the abdomen (below the intrathoracic chest cavity) dominates the distribution of ITP inside the chest. Since abdominal motion lags considerably behind the chest wall motion, the ITP can be sub-atmospheric in some areas of the thorax while it is elevated to 20–25 mm Hg in others during each compression cycle. This mechanism is exploited by the current invention in a novel approach to create what can be called "hydraulic amplification" of a thoracic pump.

There is a need for an external chest compression system that is effective in unloading the heart of a patient suffering heart failure, and is synchronous with heart systole. Such a chest compression system would have considerable advantages over all (invasive or external) counterpulsation methods because: (a) external chest compression methods do not operate during diastole and therefore are not limited by the increase of the heart rate that often follows heart failure and tends to reduce the duration of diastole, and (b) these methods do not require prediction of the beginning of the next heart cycle time intervals (required for IABP or external leg counterpulsation) that is complicated by arrhythmia that is often associated with heart failure.

External chest compression methods have the potential of not only unloading the heart, but they have the capability of propelling blood forward out of the heart and adding external mechanical energy to the heart ejection process. In contrast, counterpulsation methods do not propel blood out of the heart and do not add energy to the heart. With counterpulsation methods, the useful work to move blood is performed by the heart itself.

Although at least some of the advantages of the chest compression method were known since the mid-1970s, prior attempts to develop a usable cardiac assist treatment using external compression of the upper body have not succeeded for a variety of reasons. The principal among these are believed to be:

(a) Difficulty of finding a method that will allow generation of substantial or 'clinically significant' blood flow by applying pressure levels that the conscious patient can tolerate.

(b) Difficulty in synchronizing compressions with the beating heart, and in applying sufficient external pressure at the relatively rapid and variable cycle rates needed by a failing heart.

It was perceived by early developers that high pressures had to be applied to the chest to generate substantial blood flow. For example, U.S. Pat. No. 4,971,042 describes a cardiac assist cuirass that applies pressures as high as 250 mm Hg to the chest of a patient. In tests conducted by applicants, the application of as little as 70 mm Hg compression to the chest made the human volunteers very uncomfortable and caused substantial pain. In addition to high pressures, prior external thorax compression methods suffered from the notions that a cardiac assist treatment required: (a) simultaneous chest compression and lung ventilation, and/or (b) abdominal binding or compression of the abdomen in combination with chest compression. For example, U.S. Pat. No. 4,397,306 ('306) discloses an integrated system for cardiopulmonary resuscitation and circulation support which combines ventilation at high airway pressure simultaneous with chest compression. In addition, the system disclosed in the '306 patent tightly binds the abdomen to cause substantial amounts of abdominal pressure during chest compression, which is combined with negative diastolic airway pressure ventilation to move greater amounts of blood into the chest during diastole.

Ventilation of the lungs, which may in theory be useful, does not work well in practice. The difficulties encountered with lung ventilation include:

a) Inflating the lungs rapidly to substantial pressure levels required intubation that is a difficult and painful procedure.

b) When inflating lungs rapidly to substantial pressure levels fragile lung structures can be easily damaged.

c) While lungs can be inflated rapidly, it is practically impossible to deflate them equally rapidly without collapsing the airway. This led to dangerous 'trapping' of the air in the lungs.

In addition, the inability of synchronized ventilation to follow high heart rates is described in U.S. Pat. No. 5,020, 516.

Moreover, abdominal binding does not provide the expected amplification of ITP. Applicants, in connection with the present invention, recognized that abdominal binding does not increase the ITP. At the time of the invention, abdominal bindings were viewed as beneficial and it was not understood why they were counterproductive. Abdominal bindings appeared to be useful in restraining the abdomen to prevent the chest cavity from bulging into the abdomen while compressive forces were applied during chest compression. By restraining the abdomen and preventing bulging of the thorax, the increase in ITP would be elevated which should improve the cardiac assist treatment.

However, applicants found that while abdominal restraints did amplify the pressure in the chest, blood flow actually went down when using abdominal restraints. Prior to applicants' invention, Dr. Gruben speculated that during CPR at high compression rates, abdominal motion dominates the distribution of blood pressure in the chest. Dr. Gruben also discovered that when the abdomen was bound this phenomenon disappeared and the pressure distribution became uniform. However, Dr. Gruben had no means of measuring blood flow and never investigated the effects of unrestricted abdominal motion on blood flow.

An ineffective lung inflation plus abdominal binding approach is shown in U.S. Pat. No. 4,424,806, which discloses simultaneous lung inflation and abdominal compression. Another example of a prior cardiac assist treatment using "enhanced" external compression by a vest with inflatable bladders is shown in U.S. Pat. No. 5,490,820 ('820 patent). The '820 patent describes a vest assist device having multiple bladders arranged around the chest of a patient such that one set of bladders is positioned over the front of the chest, and other bladders are positioned at the sides of the chest. According to the system disclosed in the '820 patent, the bladder at the front of the chest (anterior bladder) is inflated when the ECG instrument monitoring the heartbeat detects the dicrotic notch in the arterial pressure waveform. The inflated anterior (front) bladder is supposed to flatten the chest and generate positive intrathoracic pressure—increase diastolic aortic, and, as a result, coronary perfusion pressure. The anterior bladder remains inflated until the onset of the systole portion of the heart cycle. At the onset of systole, the anterior bladder is deflated and the lateral (side) bladders are inflated to help restore the chest shape and generate negative intrathoracic pressure during systole—afterload reduction.

Inflatable vests have been unsuccessfully proposed for cardiac assist. Suggestions have been made that vests initially designed for cardiopulmonary resuscitation (CPR) could be adapted for vest assist. For example, U.S. Pat. No. 4,928,674 (the '674 patent) discloses a CPR vest that was a precursor to the present invention. The vest system disclosed in the '674 patent generates cyclic fluctuations in intrathoracic pressure primarily for CPR—not cardiac assist. However, the '674 patent makes a passing reference to cardiac vest assist by stating that vest inflation can be synchronized to an external signal, such as, a processed electrocardiograph, to assist a failing but still-beating heart.

Cardiac assist treatment is unlike (CPR). Cardiac assist treatment is done while the heart is still beating. The treatment assists the beating heart in moving blood through the vascular and coronary systems. CPR is done after the heart has failed and stopped beating. CPR (unlike cardiac assist) provides the sole pumping action for moving blood in the vascular system of a patient while the heart has stopped beating on its own.

Cardiac assist is technically more difficult than CPR because the cardiac assist must be synchronized with the beat of the heart. If not synchronized to the heart, cardiac assist would be counter-productive and potentially harmful to the patient. Since there is no heartbeat with CPR, there is no need to synchronize the chest compression done during CPR with a heartbeat. The problems associated with synchronizing with a heartbeat have been a particular problem associated with cardiac assist treatments.

Cardiac assist systems using inflatable vests that provided external compression were the subject of a limited number animal and human tests conducted at The Johns Hopkins University, Maryland, U.S.A. These experiments were successful in animals but, in general, not in humans. In 1988, Johns Hopkins University reported successful application of the vest in only two human patients over two years. The University attributed these failures to the inability of the equipment to: (a) support patients with heart rates greater that 75–80 beats-per-minute (bpm), and (b) difficulty synchronizing to the ECG signal when the vest was running. While improvements were made to the apparatus between 1989 and 1993, they did not remedy the reported problems. In 1992, Johns Hopkins' investigators reported that no new human patients were successfully supported by the new apparatus in spite of several generations of changes and multiple attempts.

Prior animal experiments using external compression to assist a beating heart were successful only because the natural ability of the animal's heart to pace itself was destroyed in these experimental preparations and an external electric pacing signal was used to stimulate heart contractions at a desired rate. The same signal used to stimulate the heart was used to trigger the assist apparatus in anticipation of heart contractions.

Prior to the present invention, there were no known methods or apparatuses that had been successfully used to provide cardiac assist for humans. In particular, prior to the present invention it is believed that there were no known:

a) Successful techniques for synchronizing a vest assist system to a beating heart in humans;

b) Vest assist systems that would substantially improve blood flow without exceeding tolerable force levels on the chest of a patient;

c) Vest assist systems that could achieve the objectives of sup-paragraphs (b) and (c) without artificially manipulating a patient's airway and using synchronized lung inflation therapy.

There was a long-felt need for a non-invasive therapy for providing cardiac assist. There are hundreds of thousands of patients suffering from heart failure in the United States each year. Many more patients are suffering from heart failure in other countries. The conventional treatment for heart failure is surgery, including insertion of an IABP catheter. A non-surgical approach to treating heart failure would be safer for the patients suffering from heart failure and less costly. Moreover, non-surgical treatments may be done outside of the intensive care units of hospitals, which are already over-crowded and extraordinarily expensive. A better treatment for heart failure would not require surgery or an intensive care unit of a hospital, but would still provide effective treatment and, hopefully, a cure for heart failure.

SUMMARY OF THE INVENTION

The present invention is a method and apparatus for applying external compression to assist a beating heart. The compression is applied to a patient's thorax, preferably with an inflatable vest. The vest is inflated at the beginning of the systole phase of the heart cycle. The inflation of the vest is synchronized with heart compression. The inflation of the vest increases the intrathoracic pressure within the patient to force blood out of the left ventricle of the heart and out of the aorta. The vest is deflated at the beginning of the diastole period of the heart cycle to allow blood to return into the thorax and into the heart.

In the present invention, the vest inflation is triggered by the R-wave of the ECG signal on a real-time basis. If the heart speeds up, then the triggering of the vest inflation and deflation also occurs more frequently to keep up with the heart. The heartbeat is sensed by ECG electrodes placed on the patient. The electrodes detect a surface electrical signal that is processed by an electrocardiographic instrument to generate an electrocardiogram (ECG) signal. The ECG signal has certain signature characteristics, such as the QRS wave that indicates the onset of the systole phase and ventricular contraction. When the R wave in the ECG signal is detected, a trigger signal is sent to start inflating the vest. A computer controller processes the ECG signal and detects the QRS wave using relatively-simple band-pass filtering techniques. The controller triggers the inflation and deflation of the vest, by activating a valve associated with the vest. The controller can automatically adjust the inflation period for the vest.

The vest is rapidly inflated to trap air in the lungs and to provide a rapid pressure rise in intrathoracic pressure. The vest is inflated within 100 to 150 milliseconds of the R wave.

DETAILED DESCRIPTION OF THE INVENTION

FIGS. 1A to 1F are a series of diagrams showing a patient 100 undergoing cardiac assist treatment. FIG. 2 is a diagram that presents a chart comparing blood pressure in the left ventricle of the heart, in the aorta and in the vest, and a chart of an ECG signal for one heartbeat. FIG. 2 also shows by brackets the different stages of a heartbeat cycle. Each of the two charts of FIG. 2 have time in milliseconds as their abscissa.

Figure 1A:
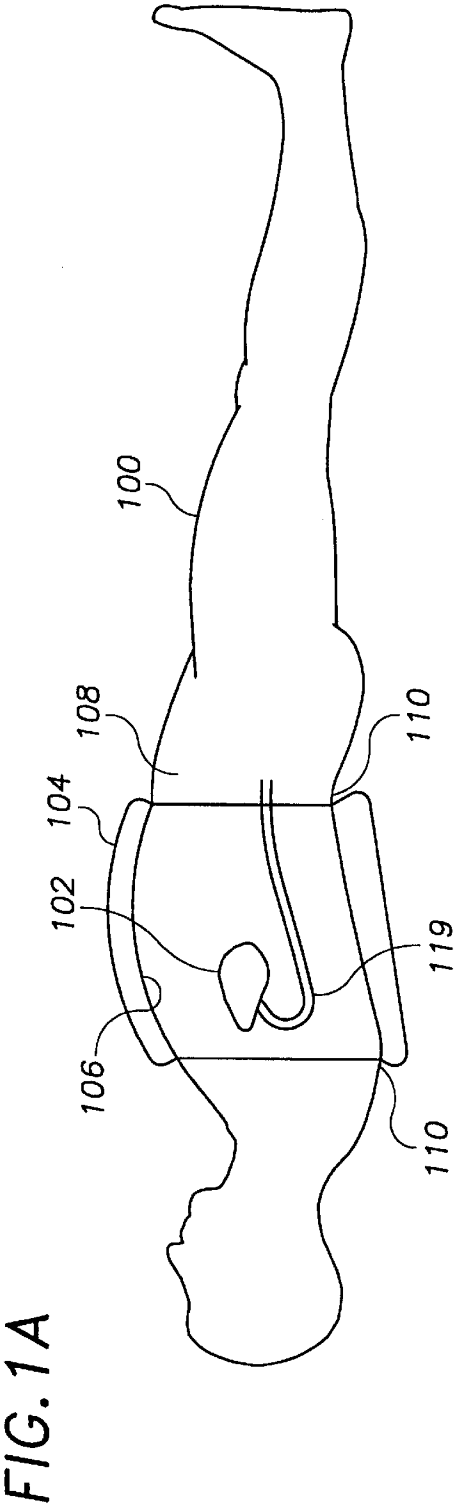
FIGS. 1A to 1F are diagrams showing the six stages of cardiac assist using an inflatable vest.
Figure 2:
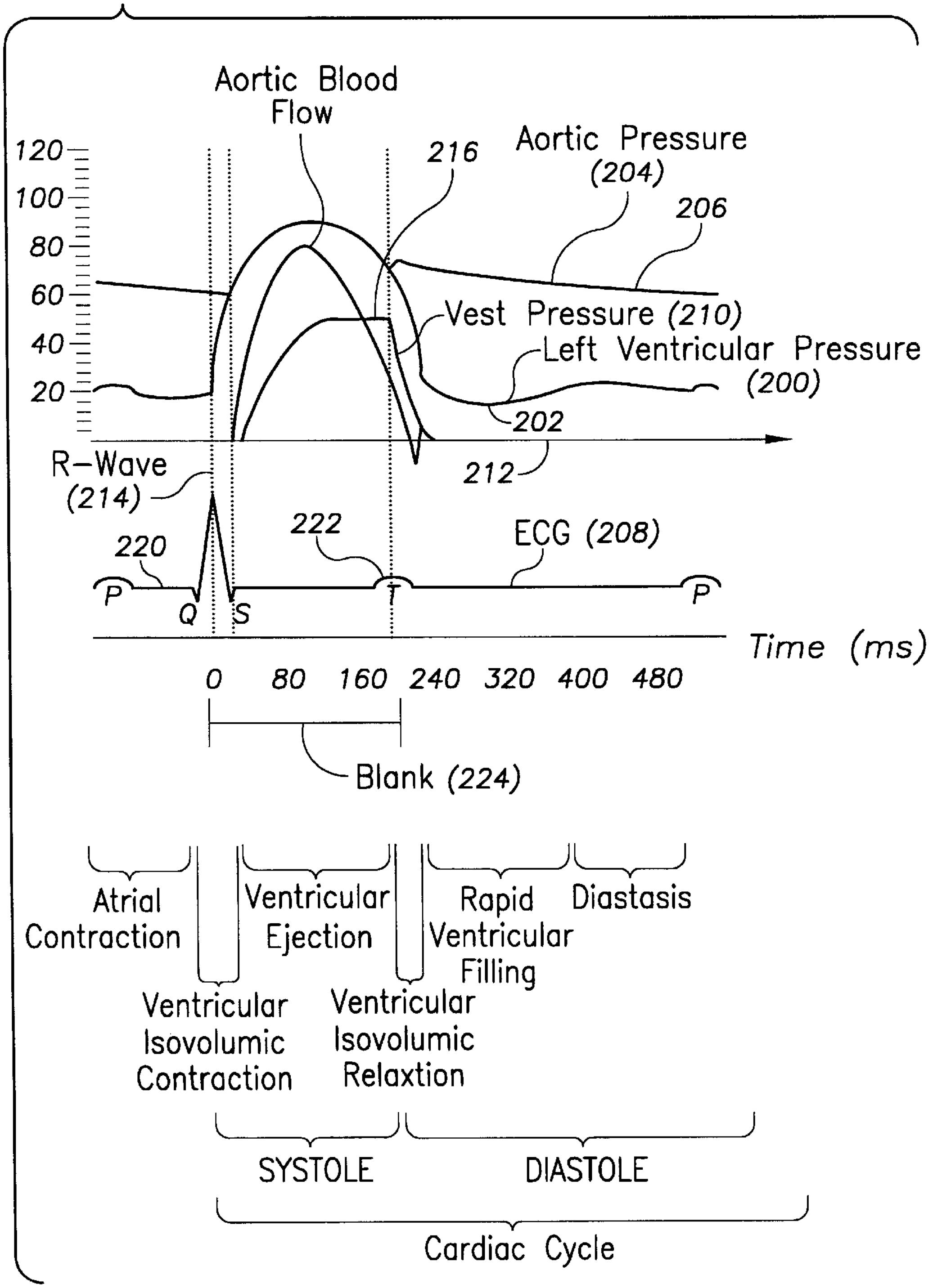
FIG. 2 is a chart showing aortic blood pressure and left ventricular chamber pressure as compared to the vest pressure, where all pressures are shown as a function of time, and a second chart showing an electrocardiogram (ECG) signal as a function of time.

FIG. 1A shows the late diastole rest state of the heart 102 of a patient 100. In this rest state, the chambers of the heart, including the left ventricle, are being refilled with blood. The vest 104 is completely deflated, the chest wall 106 of the patient is fully expanded and the patient's abdomen 108 is not moving. The vest surrounds the patient's thorax 110, but does not restrict the abdomen. The vest is shown as surrounding the thorax in FIG. 1A. To better illustrate other features, the vest is not shown as surrounding the thorax in the other figures of FIG. 1, but in fact the vest always surrounds the thorax. During the diastole period, blood also flows through the coronary arteries and the heart muscle. This blood flow to the heart muscle is crucial to the well being of the heart.

FIG. 2 shows that the pressure in the left ventricle (LV) 200 chamber of the heart is at the lowest level 202 for the entire heartbeat cycle. Because of the low pressure during diastole, the LV fills with blood. The pressure in the aorta 204 (downstream of the left ventricle) is also at a relatively-low state 206, but not as low as the LV pressure. There is minimal electrical activity of the heart during the diastole rest state. In addition, the vest has fully deflated and the vest pressure 210 is minimal 212 during the diastole period. The vest 104 is deflated to reduce intrathoracic pressure 112 on the heart while blood is filling the heart chambers and while blood is flowing through the coronary arteries to the heart muscle.

While the heart is in the diastole rest state, the heart muscle receives blood from the coronary arteries. This blood flow to the heart muscle is critical to sustaining the health of the heart. While pumping blood, the heart inhibits its own blood supply due to the contraction of the heart muscle. As the heart muscle contracts, coronary blood flow to the left ventricle chamber of the heart is throttled by the tense state of the heart muscle. Only after the heart relaxes, can blood flow into the heart muscle.

A normal heart will have a relatively-long diastole period, e.g., 400–500 ms, but a failing heart will purposefully shorten its rest period. A failing heart works harder to maintain vascular blood flow by increasing its heartbeat rate and substantially reducing the diastole period. The failing heart sacrifices its own blood flow to maintain vascular flow. A purpose of the present invention is to relieve some of the load on a failing heart, so that the heart may increase its own blood flow by reducing its beat rate and its diastole period.

The present invention improves blood flow to the heart muscle by assisting the relaxation of the heart muscle. As the heart contracts to pump blood, the muscle fibers in the heart become tense to bind the layers of the muscle together. Releasing the tension in the heart muscle during the diastole period aids in expanding, i.e., relaxing the heart and the left ventricle. As the heart muscle expands, a suction is formed in the chambers of the heart that draws in blood to those chambers. The "ventricular suction" effect is great in the thick left ventricle, where intraventricular pressure in a healthy heart can decrease several mm Hg below atmospheric pressure, due to the relaxation and expansion of the heart muscle.

The vest enhances the ventricular suction effect. The vest increases the compression of the heart during the ventricular contraction (systole) period of the heartbeat. Tension in the contracting heart muscle is increased by the vest which increases the compressive pressure on the heart. When the vest is deflated, the rib cage recoils like a released spring and reduces pressure on the heart. The rib cage surrounds the heart and great vessels among other organs. When the pressure in the vest is rapidly removed, the recoiling spring—rib cage—creates a negative pressure (intrathoracic) inside the chest in the space surrounding the heart (see FIG. 1E). The rapid deflation of the vest facilitates "ventricular suction", assists with the filling of the heart with blood and increases the pressure gradient across the heart muscle. Accordingly, the vest increases the flow of oxygenated blood from the aorta, to the inner layers of the heart muscle. In addition, when the load on the heart is reduced, due to the vest, the left-rear ventricle of the heart becomes less distended. This results in better utilization of the heart's ability to contract, ejection of blood becomes more complete and the intraventricular pressure at the end of diastole is reduced.

Figure 1B:
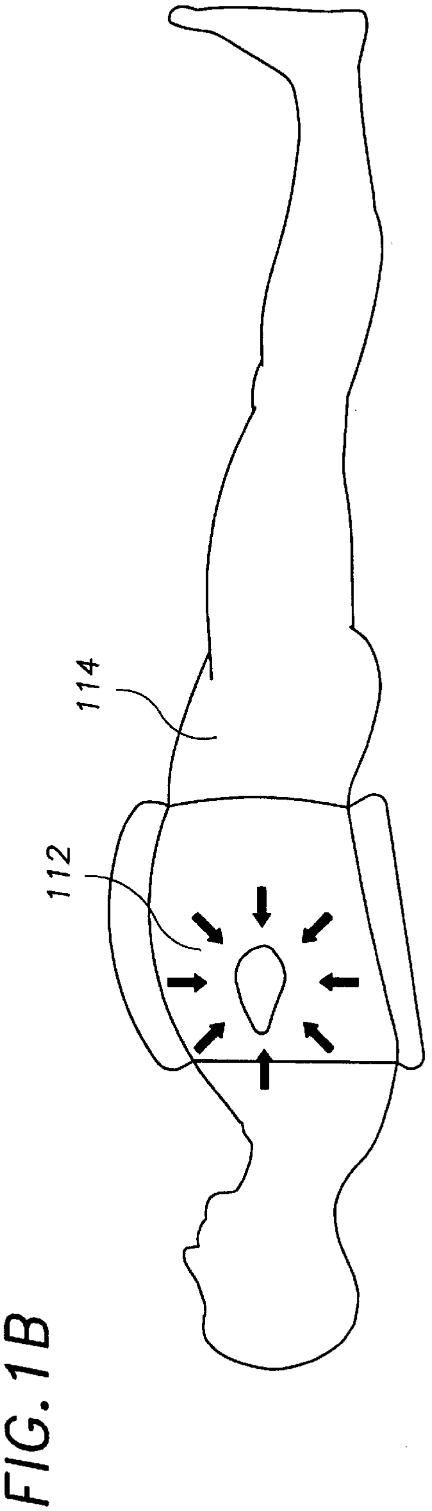
Figure 1C:
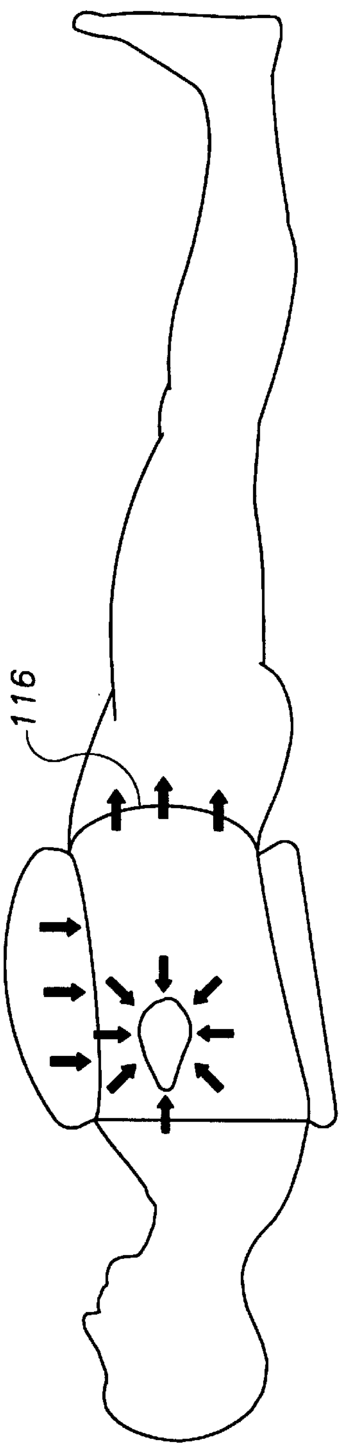

As shown in FIG. 1B, to assist in the ejection of blood from the heart, the vest 104 is inflated to apply pressure on the patient's thorax 110. The vest inflation compresses the chest and thorax, so as to increase the intrathoracic pressure that is applied to the heart, arteries within the thorax and other internal organs in the thorax. As the vest is inflated, the left ventricle contraction of the heart is assisted by an increase in intrathoracic pressure 112 in the tissue surrounding the heart. Accordingly, useful external work is performed by the vest to help the heart empty the left and right ventricles.

The inflation of the vest (and corresponding compression of the thorax) also assists the beating heart by increasing the pulsations of blood pressure and blood flow in the aorta, coronary arteries, carotid and other arteries. The vest causes the left ventricular (LV) 200 pressure to have higher maximums and lower minimums than would occur without the vest. The increased pulsatility of the blood flow plays important role in vital organ and particularly heart perfusion. Sudden changes in blood flow are believed to increase the shear-stress on the endothelium (inner layer of tissue in the blood vessels) within the blood vessel system, liberating Endothelial-Derived Relaxing Factor (EDRF), a powerful compound that causes relaxation of vascular smooth muscle. The process of EDRF release causes additional capillaries to open, increasing blood flow and relief of ischemic pain. Accordingly, by increasing the pulsatility of blood pressure and flow, even if the average blood flow level stays the same, the vest 104 can be beneficial to patients with failing hearts. External systolic compressions by the vest of the chest invariably increases blood pressure and flow pulsations. These compressions stimulate the release of salutary chemical agents that relax vasculature and improve coronary blood flow by reducing resistance even if the pressure gradient stays the same. Moreover, vest assist can be used to increase pulsatility of blood flow by itself or in combination with continuous flow assist devices.

The vest 104 pressure affects the aorta as well as the left ventricle. The vest forces blood out of the entire thorax area 110 of the body. The blood is forced out of the heart and out of the neighboring aorta and other arteries within the thorax. By helping to empty the aorta, the vest reduces the amount of blood that remains in the aorta after each contraction of the heart. Without the vest, the blood that remains in the aorta must be pushed solely by the heart into the vascular system when the heart contracts and empties the LV. The blood remaining in the aorta is an impedance that increases the work that the LV must perform during contraction. With the vest, there is relatively little blood left in the aorta when the LV contracts. Accordingly, the vest reduces the afterload impedance that the heart must overcome. The impedance due to the blood remaining the aorta, called the "afterload", can be thought of as the amount of energy that the ventricle will need to spend to eject blood.

As shown in FIG. 1B, the inflation of the vest 104 occurs during the early systole period of each beat of the heart. The systole period is the contraction of the left ventricle of the heart which forces blood out of the heart and into the aorta. Heart systole is measured as the duration between the onset of left ventricle contraction (rapid buildup of pressure), and the moment when the aortic valve closes and the flow of blood stops from the left ventricle into the aorta.

The inflation of the vest is triggered by the beat of the heart. The heart is monitored by an electrocardiogram (ECG) instrument (FIG. 3) which includes electrodes 328 fastened to the patient that detect the electrical activity of the heart. The ECG instrument can output a graph of the electrical activity of the heart. FIG. 2 shows an exemplary ECG signal 208 showing the cyclical electrical activity of the heart from which the beating action of the heart is evident.

The vest inflation may start within the first 100 ms of each heart cycle, where the start of the cycle is the beginning of the systole period. The vest inflation system is triggered by detection of the R-wave 214 in the ECG. Pressure in the vest starts to build up approximately 30–40 ms after the R-wave is detected, in virtual synchrony with contraction of the left ventricle of the heart. Moreover, the vest inflation is in real time synchrony with the ECG signal.

The vest is rapidly inflated and applies pressure to the chest wall 106. During the first 40–50 milliseconds of vest inflation, pressure in the thorax 110 of the patient builds up rapidly. The compression of the thorax will cause the breathing airway to the lung of the patient to collapse when the intrathoracic pressure reaches levels in excess of approximately 10–15 mm Hg. By collapsing the airway, the exhalation of air from the lungs is stopped and air is trapped in the lungs. The air trapped in the lung contributes to the build up of pressure inside the chest during vest inflation. If air were allowed to exhaust from the lung, then the deflation of the lungs would undermine the ability of the vest to increase intrathoracic pressure. Accordingly, by rapidly inflating the vest, the intrathoracic pressure is also rapidly increased, due in part to air being trapped in the lungs and the inertial resistance of the abdomen.

During rapid vest inflation the abdomen 114 (below the thorax) does not immediately move in response to the compression of the thorax. The organs in the thorax and abdomen dynamically respond to the vest. The abdomen has a substantial inertia (mass) that prevents it from moving immediately in response to the rise in intrathoracic pressure. When the vest is inflated, the diaphragm 116, between the thorax and the abdomen, does not move immediately to relieve the pressure because the intrathoracic pressure does not immediately push against the diaphragm. The increase in intrathoracic pressure due to the vest creates a pressure wave that travels downward in the patient's body to the diaphragm.

As the intrathoracic pressure wave reaches the diaphragm 116, the diaphragm begins to moves away from the thorax. As the diaphragm moves outward, it pushes against the abdominal organs. The abdomen starts to move and accelerates in a "fluid" or wave-like fashion away from the thorax. Since the system is no longer isovolumic (diaphragm movement increases the thoracic volume), the rate of pressure buildup inside the chest is considerably reduced. Moreover, the thoracic aorta that extends through diaphragm into the abdomen is actively emptied of blood by the intrathoracic pressure wave and the simultaneous contraction of the left ventricle in the heart.

Figure 1D:
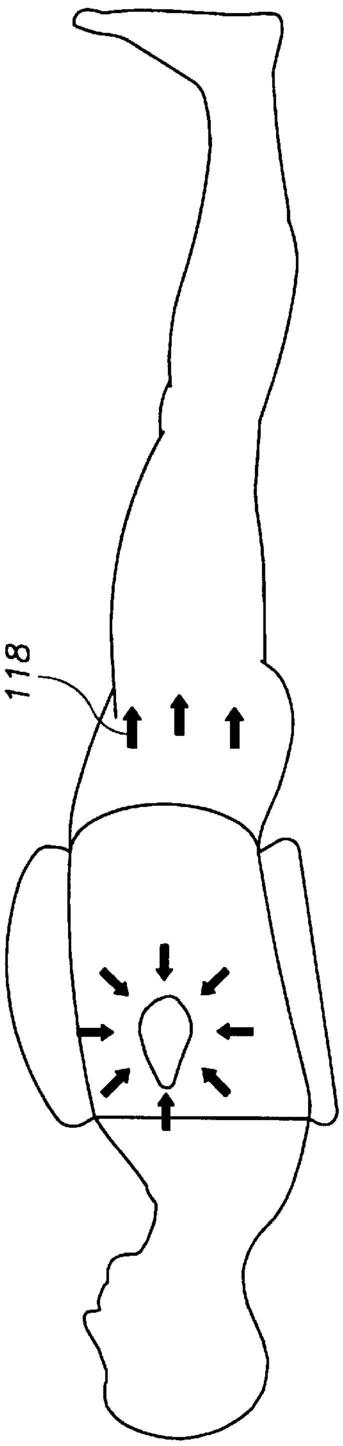

As shown in FIG. 1D, during the late systole period of the heart cycle, the vest is fully inflated and is maintained at its maximum pressure for the remainder of the systolic compression period. The chest wall stops moving inward due to the compression of the vest, but the abdomen, due to its substantial inertia, continues to move downward and is decelerating. Abdominal inertia 118 generates a negative pressure that pulls on the diaphragm. The inertia of the moving abdomen carries the abdomen away from the thorax until the tension of the abdomen and the force of inertia are equal, at which point the tension pulls the abdomen back towards the thorax. The abdomen reacts in a manner similar to a spring that is being uncoiled and will latter snap back to a coiled position.

Inside the chest the abdominal motion produces a rather counterintuitive, negative intrathoracic pressure in the middle of the external chest compression phase. This negative pressure is much stronger in the areas of the chest away from the heart and affects the aorta more than the left ventricle of the heart. Negative intrathoracic pressure at the peak of chest compression is confirmed by a short but detectable inhalation of air into the chest.

The natural frequency of the thoracic-abdominal viscoelastic model is approximately 5 Hz. The abdominal motion waveform (i.e., one full cycle of displacement from its neutral position and return) takes approximately 200 ms to complete. When the abdomen stops its "fluid" motion downward, the diaphragm and negative pressure inside the chest act as a stretched spring to bring the abdomen back to its equilibrium position. The returning abdomen generates a "reflected" pressure waveform in blood vessels and augments the pressure inside the thorax that is already elevated as a result of thoracic volume reduction by the vest. Thus, pressure augmentation by the vest reaches its peak 216 during late heart systole. At this time, the heart is in the last stage of its ejection and the increase in intrathoracic pressure assists in the emptying of the left ventricle.

Figure 1E:
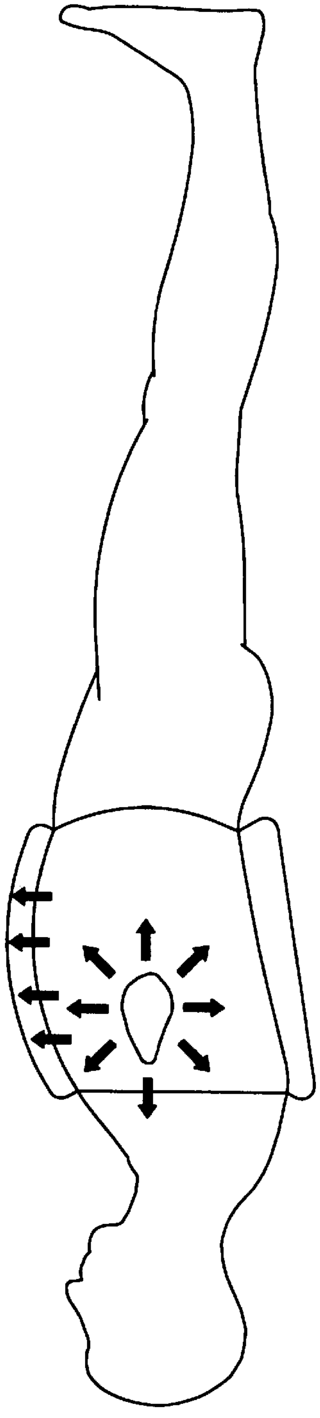

FIG. 1E represents the diastole period of the heart cycle in which there is a rapid release of the chest by deflating the vest. This part of the heart cycle corresponds to early heart diastole phase when coronary blood flow is the highest and is of paramount importance for coronary perfusion during ischemia.

After the vest compression force is removed, the chest will tend to recoil as rapidly as it can if its motion is not impeded. For this reason, the vest needs to be deflated quickly. The vest may be allowed to exhaust to the atmosphere. Alternatively, the vest can be deflated by applying a vacuum to the vest during the heart diastole period, actively collapsing the vest bladder. To rapidly deflate the vest, large bore valves and tubing that allows high air flow are used to allow air to move quickly out of the vest. Rapid vest deflation, if it occurs just after the closure of the aortic valve, can: reduce left ventricular early diastolic pressure (when coronary flow is the highest), relieve ischemia, and improve the return of venous blood to the heart and improve cardiac output.

Under normal conditions, the distribution of coronary blood flow across the heart wall is uniform. The diastolic gradient from aorta to the heart during diastole favors coronary flow. However, in the failing heart, and especially with coronary artery decease, a substantially-reduced quantity of blood is delivered to the internal layers of the heart muscle. Flow to these layers of muscle occurs predominantly during diastole and depends on the driving coronary perfusion pressure gradient. Ventricular diastolic pressure is the downstream pressure for this gradient and inhibits flow in direct proportion to its level.

In the healthy heart, left ventricular diastolic pressure is in the range of 5–15 mm Hg and presents negligible opposition to coronary flow that is driven by a diastolic aortic pressure of 60–90 mm Hg. With coronary obstruction, this driving pressure gradient can be severely reduced as blood travels forward along a clogged artery. In addition, in the failing heart, the left ventricular diastolic pressure 200 is often elevated to 15 to 35 mm Hg over the pressure of a healthy heart. Under these circumstances, small changes in ventricular diastolic pressure become one of the primary determinants of flow in sub-endocardial (internal) layers of the heart muscle.

During inflation of the vest, the rib cage behaves like a tightly compressed spring. At the end of vest chest compression, the abdomen has settled its fluid motion in a new position downward from its normal position. The diaphragm 116 has been extended by the elevated pressure in the thorax. When the pressure on the chest is rapidly released, the rib cage recoils back immediately since there is little inertia directly associated with its motion. The abdominal return motion is dominated by its mass and, due to its considerable inertia, lags behind and cannot return immediately to its normal position. The recoiling chest and lagging abdomen temporarily generates a suction inside the thorax since the rib cage is expanding and abdomen and diaphragm cannot follow quite fast enough. This suction pressure is transmitted to the heart and particularly to the left ventricle. Accordingly, the rapid deflation of the vest results in a reduction in intrathoracic pressure that achieves a beneficial decrease in ventricular diastolic pressure. In animals, early diastolic left ventricular pressure was reduced during vest release by 10–20 mm Hg, and in some instances even became negative.

The lower induced pressure in the left ventricular chamber and the relatively higher aortic pressure due to the vest is beneficial in moving blood through the coronary arteries and into the heart muscle. Because of the pressure differential between the left ventricular chamber 200 and aorta 204, blood is drawn rapidly from the aorta, through the coronary arteries and into the heart muscle. The blood flow to the heart muscle is particularly advantageous in a failing heart which is attempting to compensate for its weakness by reducing the rest time period (diastole state) during which blood is drawn into the heart muscle. By increasing the pressure difference between the heart and the aorta, the amount of blood to the heart muscle can be increased to compensate for the reduced diastole period. The more blood that can be drawn into the heart muscle, the more likely it is that the heart can break the cycle that is leading it to failure and begin to heal itself.

Figure 1F:
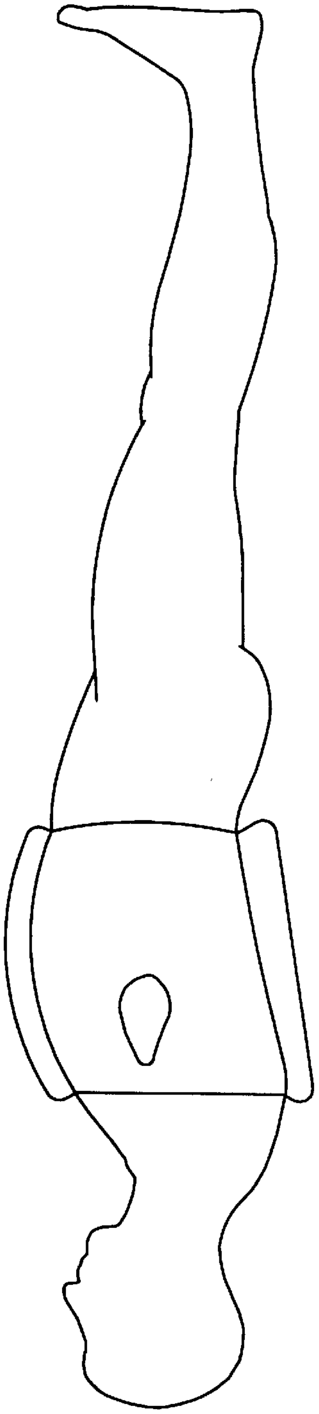

FIG. 1F shows the heart in its late diastole rest state, as does FIG. 1A. The vest is completely deflated, the chest wall is fully expanded, and the abdomen has stopped moving. The heart is being refilled by blood.

In addition, the heart ejects only as much blood as was filled into the heart during the diastole period. If the heart does not have sufficient time to refill during the diastole period, there will not be enough blood to eject during the systole period. Encroachment of the vest chest compression into the diastolic relaxation time can lead to an impeded venous blood return to the heart and negatively impact cardiac output. The vest is deflated fully and rapidly within as short a time period as possible and no longer than 50–70 ms. Accordingly, rapid deflation of the vest helps return blood back to the heart so that the heart can refill for the next ejection cycle.

When the vest compresses the chest, it also exerts considerable external pressure on lungs and pulmonary blood vessels. This compression can lead to an elevation in arterial blood pressure and to partial collapse of alveoli (tiny, thin-walled, capillary-rich sacs in the lungs where the exchange of oxygen and carbon dioxide takes place) during the compression of phase of the assist cycle. Alveoli are known to be harder to open than they are to close and, at high heart rates, the diastolic portion of the heart cycle may not leave them sufficient time to recover. A dangerous condition known as pulmonary shunt can develop when part of the arterial blood is not oxygenated (i.e., a portion of the blood circulating through the lungs passes through the section that is collapsed). This condition can be prevented in two ways. Positive End Expiratory Pressure (PEEP) ventilation can be turned on prior to vest assist if the patient has a ventilator breathing for him, as heart failure patients often do. Small amounts of positive pressure applied to the lungs between breaths will allow the lungs to stay open when the chest is compressed. Alternatively, a brief pause can be introduced every so many assist cycles for several seconds to allow the lungs to open and blood oxygenation to recover. This function can be automatic and programmed in by a physician based on the gas content ($O_2$ and $CO_2$) of the patient's blood or expired air.

Figures 1, 3:
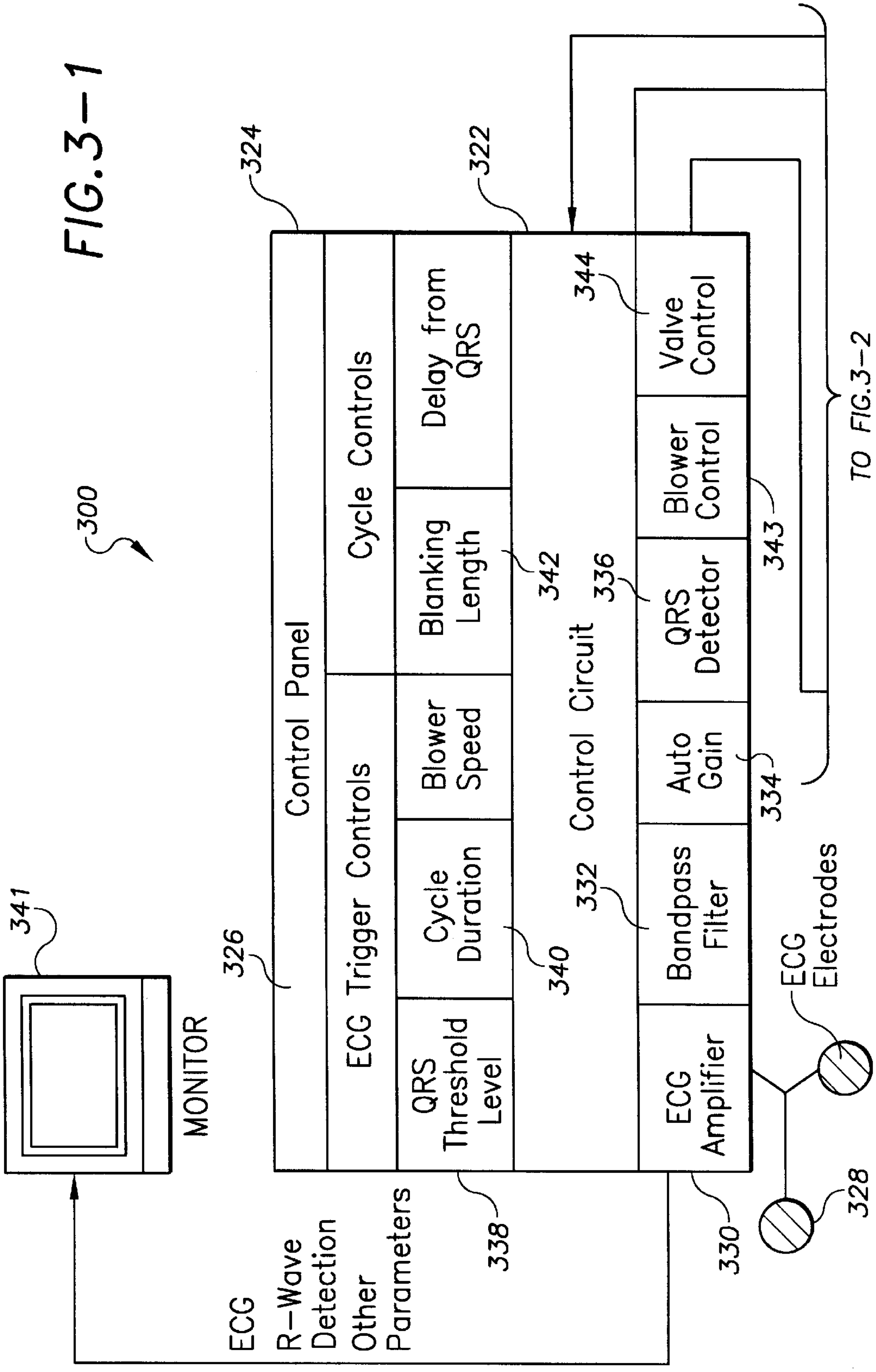
FIG. 3 is a diagram of an exemplary vest assist system with vest, blower and controller.
Figures 2, 3:
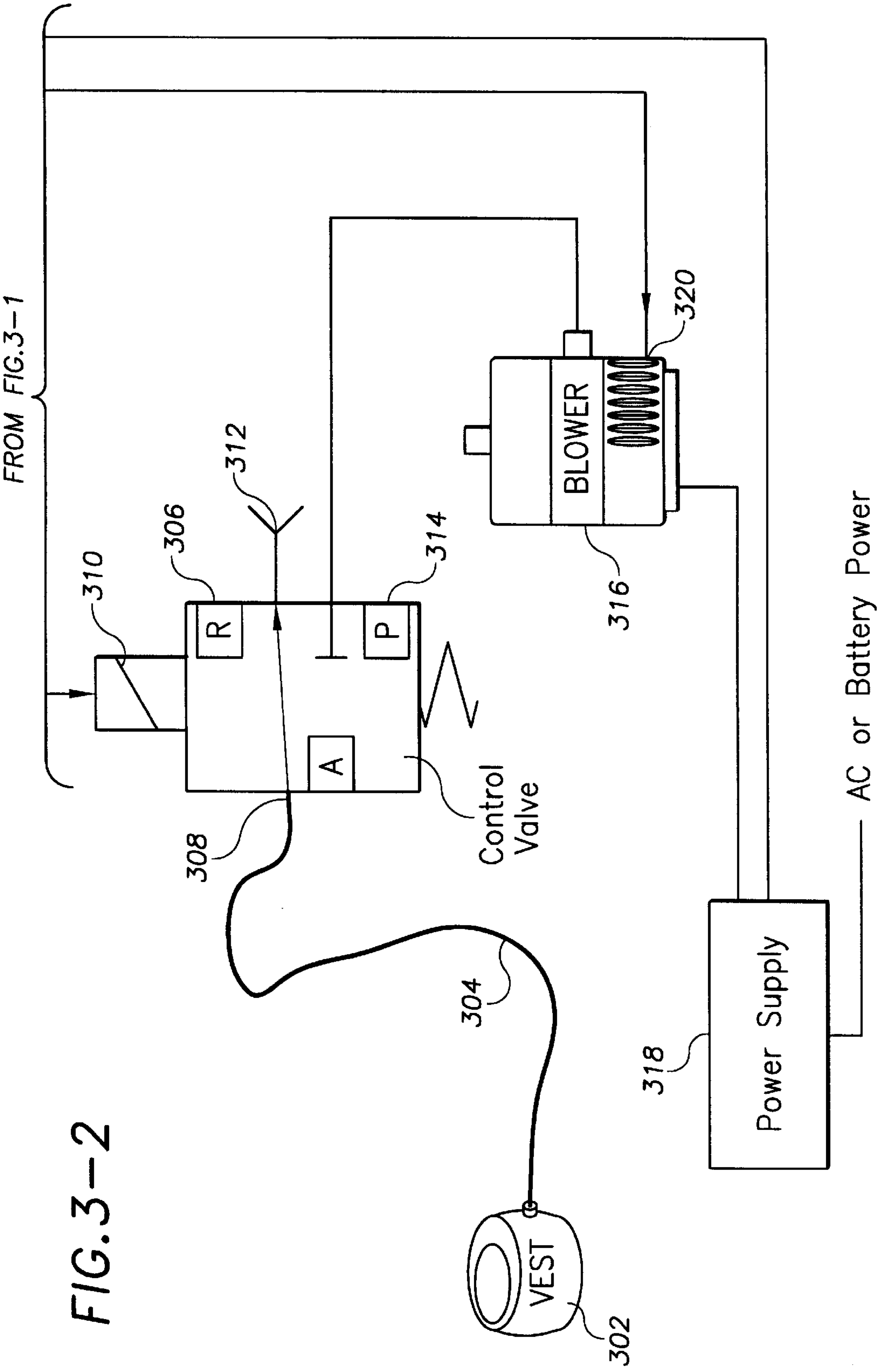

FIG. 3 shows an exemplary vest assist system 300. The system includes a vest 302 that wraps around the thorax of a patient. The vest is inflatable and is connected to an air (or other gas) hose 304. At the other end of the hose is a control valve 306 that controls the air flow to and from the vest. The control valve may include a detachable coupling 308 for the air hose 304. The valve may be operated by a computer controlled solenoid 310 that switches the valve between an exhaust port 312 (or vacuum port) and a pressurization port 314. The exhaust port may be open directly to the atmosphere or it may be connected to a vacuum source, such as the intake of the blower 316. The pressurization port is connected to a source of air pressure, such as the output of a centrifugal blower 316. The blower has a power supply 318 and receives a control signal 320 from a computer controller 322. The blower and the vest apparatus are described in co-pending and commonly-owned U.S. patent application Ser. No. 08/731,049 entitled "Cardiopulmonary Resuscitation System with Centrifugal Compression Pump", which is fully incorporated by reference. The blower may be a Windjammer 800 Watt 1-Stage High Flow blower from Ametek (Kent, Ohio). The blower design allows extremely rapid inflation of the vest of substantial size (needed for efficiency) connected by a large volume hose (needed for convenience and practicality).

The computer controller 322 may be a microprocessor controlled system having an ECG instrument, blower controls and vest controls. A control panel 324 on the microprocessor system provides a health care operator with output readings and input keys to operate the vest assist system.

The controller 322 has an ECG instrument 326 that processes electrical signals from the ECG pads 328 attached to the patient to produce an ECG signal 208. The ECG electrodes may be positioned on the left and right arms or shoulders, instead of the traditional positioning on the chest without compromising the ECG signal. By removing electrodes from the chest, the influence of chest compression on the ECG is greatly reduced. In addition, moving the electrodes facilitated the application of the vest to the patient.

The ECG instrument may include an ECG signal amplifier 330, a bandpass filter 332 and an auto gain circuit 334, to process the raw ECG signal from the electrodes 328. The R wave 214 component of the electrocardiogram (ECG) is detected in real time and without delay. The chest compressions associated with vest assist, however, do introduce artifacts in the measured ECG signal. It is believed that compression-induced artifacts are due to changes in the half-cell potential of electrodes, caused by their mechanical disturbance. The difference in changes of half-cell potentials added to the ECG and was phase-locked to the ECG (i.e. they occur synchronously with the compression).

Bandpass filtering 332 uses a fast, frequency-domain method for suppressing signal artifacts known to reside within a specific frequency band. For a typical ECG, there is significant power at each of the harmonics of the fundamental heart rate (1–3 Hz), up to roughly 50 Hz. Using Fourier analysis, the compression-induced artifacts are primarily confined to frequencies below roughly 4 Hz and the artifacts dwarf the components of the true ECG in that frequency range. Thus, filtering out the portions of the ECG that fall below 4 Hz removes the artifacts but retains the QRS complex signal 220 needed to synchronize the vest with heart ejection. The useful QRS information is contained in the frequency band that is bordering on the artifact. A high order Butterworth filter provides high selectivity and minimal delay, and is suitable for the vest assist system 300.

The ECG instrument may also include a QRS detector 336 to sense the QRS complex 220 from the processed signal obtained from the ECG electrodes. The operator may set the QRS threshold 338 and the cycle duration 340. The inflation duration is used to adjust the duration of each chest compression by the vest. Inflation duration is measured from the beginning of the vest inflation to the beginning of vest deflation. In general, optimum system operation is achieved with vest inflation corresponding exactly to heart systole. Hemodynamic monitoring can be used to adjust compression duration during operation of the system.

The operator can also set the inflation duration by using tables or nomograms. Since in the weakened heart parameters of the cardiac cycle have a tendency to become unstable, it is desirable to have a system for automatic determination of cycle parameters and adjustment of the duration of vest inflation. The adjustment of vest inflation duration is set and adjusted by a computer 346, which analyzes several previous heart cycles and predicts the best parameters, including inflation duration, for several successive heart cycles.

A safety feature is incorporated in the controller 322 that prevents the vest inflation duration 340 from lasting more than one-half (50%) of the heart cycle duration under any condition. The heart cycle can be calculated by the computer controller and averaged over several cycles so that an alarm can be issued to the operator if the duration set is too long for the current heart rate. Alternatively, the computer controller 322 may limit the duration automatically or stop chest compressions if the condition is not corrected over several consecutive cycles.

As well as establishing a reliable trigger on the R-wave, the vest assist system should not trigger on electric noise, premature heartbeats, elevated T-wave 222 and other ECG components that follow the QRS complex 220. An adjustable signal "blanking" period 224 is used to avoid the noise components following the QRS complex 220. The blanking time is set in milliseconds by the operator using a dial or other input 342 on the control panel. For example, if blanking is set to 200 ms, all spikes (e.g., T 222, and ECG components that might be mistaken for the R-wave) are ignored for 200 ms after the last triggering event. The blanking feature allows the controller system 322 to reject the majority of the noise induced momentarily by chest compressions, to reject premature heartbeats, and to prevent triggering on T-waves. If the vest were triggered prematurely (before the next R-wave), it might compress the chest during heart diastole and prevent venous blood from returning to the heart. It is recommended that the blanking time be set to 50% of the total heart cycle so that noise induced by vest compressions, amplified T-waves, as well as some premature heartbeats, will be ignored by the system.

Since the amplitude of the QRS complex of a patient's ECG can change during assist, the controller system includes an automatic gain adjustment 334 that maintains the ECG amplifier output relatively constant. In addition, to provide robust and reliable triggering of the vest 302, an adjustable R-wave threshold detection control 338 is included in the controller electronics. The threshold level is adjustable with a knob or other input on the control panel.

To ensure correct operation, the controller 322 and inflation system are used with a real time display monitor 341. The ECG signal is displayed after processing through filters, with threshold level superimposed on the ECG trace to illustrate triggering. Optionally, the vest pressure and/or blood pressure traces can be displayed on the same screen.

The intrathoracic pressure pulse 112 generated by the vest 104 is to be synchronized with the systole period. Heart systole can be from 200 to 400 ms depending on the heart rate and physical condition of the heart. Accordingly, the duration of the vest pressure pulse could be adjusted by the operator or automatically based on the patient's heart rate. For example, in a patient with a heart rate of 70 bpm, chest compression duration can be set to 400 ms; and with a patient with a heart rate of 140 bpm, it can be set to approximately 200 ms. If a real time display of blood pressure is available from a right or left heart catheter, this duration can be further adjusted based on a visual inspection of aortic, left ventricular, or pulmonary artery blood pressure augmentation during systole.

The controller 322 also has blower controls 343 to set the rotational speed of the blower that provides air to the vest and valve controls 344 that operate the valve solenoid 310 that switches the vest between inflation and deflation. In conjunction with the valve solenoid control, the controller 322 also determines the delay between the QRS and the pulse used to trigger vest inflation.

This delay adjustment is reserved for those rare instances when the operator of the device may find it desirable to increase the time between the R-wave and the onset of the vest inflation. When the delay is set to zero, vest inflation occurs 30–50 milliseconds after the R-wave. In the normal heart, this corresponds to the beginning of left ventricular contraction. Infrequently, a clinical condition is encountered where the onset of the ventricular contraction is delayed from the R-wave by more than 50 milliseconds. In such cases the delay adjustment can be used to adjust the timing of vest inflation accordingly.

The vest assist system 300 is efficient and safe. The vest 302 generates intrathoracic pressures (pressure inside the thorax) of approximately 20–35 mm Hg, using vest pressures of 35–70 mm Hg, which is substantially less than had been used in prior art vest assist systems which used vest pressures of 100–150 mm. The vest maximizes the utilization of the vest-chest contact area by completely covering the thorax area of the patient. The vest also minimizes the loss of energy in the vest by using inextensible materials and vests designed with side-walls covered by the vest belt to prevent pressure-wasting bulging of the vest air bladder. The vest 302 operates effectively at vest pressures of 35–70 mm Hg and is disclosed in detail in the U.S. patent application Ser. No. 08/404,442, which is incorporated by reference.

The inflation of the vest is synchronized with the heart cycle. Heart failure in humans is frequently accompanied by a rapid heartbeat. This is a natural compensation mechanism of the body—an attempt to maintain blood flow to vital organs by increasing the number of heart ejections per minute when the amount of blood moved by each ejection has been reduced by disease. Under such circumstances, the heart rate can reach 140–160 bpm. At 150 bpm, each heart cycle will last only 400 ms. Of this 400 ms, approximately 200 ms will be allocated for heart systole (contraction) and 200 for diastole (relaxation) during which time blood flows into heart muscle. For comparison, IABP techniques and leg counter-pulsation systems are commonly perceived as ineffective at heart rates above 100 bpm and are not recommended by manufacturer at heart rates of over 120 bpm.

Because the heartbeat rate may be relatively high, the vest assist system 300 actively starts compressing the chest within approximately 40 ms after the R wave 214 of the surface ECG signal. In the vest assist system, rapid inflation in response to the R wave is achieved by: (a) use of “minimum delay” ECG processing system; (b) fast acting pneumatic valves with minimal mechanical lag; (c) large bore pneumatic hose 304 to connect the vest to the inflation system; and (d) a high flow blower 316 that runs continuously and rapidly pumps air into the vest when the valve 306 is switched to the inflation mode.

The invention has been described in what is presently considered to be the most practical and preferred embodiment. The invention is not limited to the disclosed embodiment(s). The invention is broader than the disclosed embodiment. It covers the various modifications and equivalent arrangements included within the spirit and scope of the appended claims.

What is claimed is:

1. A device for cyclically compressing the chest of a patient, said device comprising:

compression means for cyclically compressing and decompressing the chest of the patient through a plurality of compression cycles;

sensing means for detecting a predetermined triggering event during a heartbeat of the patient and for providing a triggering signal corresponding to the triggering event; and a controller for controlling the compression means and for receiving the triggering signal from the sensing means, said controller being programmed to initiate a compression cycle upon receipt of the triggering signal, said controller further programmed to ignore signals from the sensing means for a predetermined period after receipt of the triggering signal.

2. A device for cyclically compressing the chest of a patient, said device comprising:

an inflatable vest for cyclically compressing and decompressing the chest of the patient through a plurality of compression cycles;

an electrocardiogram for detecting a predetermined triggering event during a heartbeat of the patient and for providing a triggering signal corresponding to the predetermined triggering event, the triggering signal comprising at least a first triggering signal and a second triggering signal; and a controller for controlling the inflatable vest and for receiving the triggering signal from the electrocardiogram, said controller being programmed to initiate a compression cycle upon receipt of the first triggering signal, said controller further programmed to ignore the second triggering signal from the electrocardiogram if the second triggering signal occurs within a predetermined period after receipt of the first triggering signal.

3. A device for cyclically compressing the chest of a patient, said device comprising:

an inflatable vest for cyclically compressing and decompressing the chest of the patient through a plurality of compression cycles;

an electrocardiogram for detecting a QRS-wave during a heartbeat of the patient and for providing a triggering signal corresponding to the QRS-wave, the triggering signal comprising at least a first triggering signal and a second triggering signal; and a controller for controlling the inflatable vest and for receiving the triggering signal from the electrocardiogram, said controller being programmed to initiate a compression cycle upon receipt of the first triggering signal, said controller further programmed to ignore the second triggering signal from the electrocardiogram if the second triggering signal occurs within a predetermined period after receipt of the first triggering signal.

* * * * *